US012762409B1

(12) United States Patent
Reiman et al.

(10) Patent No.: US 12,762,409 B1
(45) Date of Patent: Oct. 13, 2026

(54) PREDICTING PROTEIN STRUCTURAL STABILITY USING INTERMEDIATE OUTPUTS OF A PROTEIN STRUCTURE PREDICTION NEURAL NETWORK

(71) Applicant: GDM Holding LLC, Mountain View, CA (US)

(72) Inventors: David Reiman, Santa Cruz, CA (US); John Jumper, London (GB); Raphael John Lamarre Townshend, Menlo Park, CA (US); Simon Kohl, London (GB); Andrew W. Senior, London (GB)

(73) Assignee: GDM Holding LLC, Mountain View, CA (US)

( * ) Notice: Subject to any disclaimer, the term of this patent is extended or adjusted under 35 U.S.C. 154(b) by 1134 days.

(21) Appl. No.: 17/400,976

(22) Filed: Aug. 12, 2021

Related U.S. Application Data

(60) Provisional application No. 63/082,313, filed on Sep. 23, 2020.

(51) Int. Cl.

| | |
|---|---|
| ***G06N 3/084*** | (2023.01) |
| ***G06F 18/21*** | (2023.01) |
| ***G06N 3/045*** | (2023.01) |
| ***G16B 30/20*** | (2019.01) |
| ***G16B 40/00*** | (2019.01) |

(52) U.S. Cl.
CPC ............. *G06N 3/084* (2013.01); *G06N 3/045* (2023.01); *G16B 30/20* (2019.02); *G16B 40/00* (2019.02); *G06F 18/217* (2023.01)

(58) Field of Classification Search
CPC .......... G06N 3/084; G06N 3/045; G06N 3/08; G06N 3/0455; G16B 40/00; G16B 30/20; G06F 18/217; G06F 18/2193
See application file for complete search history.

(56) References Cited

U.S. PATENT DOCUMENTS

| | | | |
|---|---|---|---|
| 8,775,341 B1 | 7/2014 | Commons | |
| 9,015,093 B1 | 4/2015 | Commons | |
| 10,546,237 B2 | 1/2020 | Heifets et al. | |
| 2017/0032079 A1* | 2/2017 | Fleishman ..... | C12Y 201/01037 |
| 2017/0329892 A1* | 11/2017 | Fan ........................ | G16B 15/00 |
| 2019/0259470 A1 | 8/2019 | Olafson | |
| 2019/0287515 A1 | 9/2019 | Li et al. | |
| 2019/0391158 A1 | 12/2019 | Kido | |
| 2021/0210159 A1 | 7/2021 | Grigoryan | |
| 2021/0304847 A1* | 9/2021 | Senior ............... | G06F 18/24147 |

FOREIGN PATENT DOCUMENTS

| | | |
|---|---|---|
| CN | 107622182 A | 1/2018 |
| CN | 111667884 A | 9/2020 |

OTHER PUBLICATIONS

Gibney, B R et al. Synthesis of novel proteins. Current opinion in chemical biology vol. 1,4 (1997): 537-42. (Year: 1997).*
Yang, Yang, et al. "ProTstab predictor for cellular protein stability." BMC genomics 20.1 (2019): 804. (Year: 2019).*
Li, Xiuming, et al. "Deepchemstable: chemical stability prediction with an attention-based graph convolution network." Journal of chemical information and modeling 59.3 (2019): 1044-1049. (Year: 2019).*
Abbasi et al., "Modeling Teacher-Student Techniques in Deep Neural Networks for Knowledge Distillation," 2020 International Conference on Machine Vision and Image Processing, Feb. 2020, pp. 1-6.
International Search Report and Written Opinion in International Appln. No. PCT/EP2021/072552, dated Dec. 10, 2021, 23 pages.
Senior et al., "Improved protein structure prediction using potentials from deep learning," Nature, Jan. 2020, 577(7792):706-710.
youtube.com "[Live Machine Learning Research] Plain Self-Ensembles (I actually Discover Something)—Part 1," Jul. 6, 2020, retrieved on Dec. 10, 2021, retrieved from URL<https://www.youtube.com/watch?v=z_3Qv4In2ac>, 2 pages.
Zhang et al., "Be Your Own Teacher: Improve the Performance of Convolutional Neural Networks via Self Distillation," 2019 IEEE/CVF International Conference on Computer, Oct. 2019, pp. 3712-3721.
Chou et al., "Simulated annealing approach to the study of protein structures," Protein Engineering, Design and Selection, Aug. 1991, 4(6):661-667.
Koga et al., "Principles for designing ideal protein structures," Nature, Nov. 2012, 491(7423):222-227.
Putinseva, [online], "How to build a platform to design new protein therapeutics," Presented at LondonAI, May 21, 2020, retrieved on Nov. 4, 2021, <https://www.youtube.com/watch?v=njbcG9jFFVM>, 2 page [Video Submission].
Strauch et al., "Computational design of trimeric influenza-neutralizing proteins targeting the hemagglutinin receptor binding site," Nat Biotechnol, Jul. 2017, 35(7):667-671.
Zhang et al., "Protein structure optimization using improved simulated annealing algorithm on a three-dimensional AB off-lattice model," Computational Biology and Chemistry, Apr. 2020, 85:107237.
Neal, "MCMC using Hamiltonian dynamics," Ch. 5, Handbook of Markov Chain Monte Carlo, Chapman & Hall/ CRC Press, 2011, 51 pages.

(Continued)

*Primary Examiner* — Olivia M. Wise
*Assistant Examiner* — Keenan Neil Anderson-Fears
(74) *Attorney, Agent, or Firm* — Fish & Richardson P.C.

(57) ABSTRACT

Methods, systems, and apparatus, including computer programs encoded on a computer storage medium, for predicting structural stability of a protein specified by an amino acid sequence. In one aspect, a method comprises: processing an input comprising a representation of the amino acid sequence of the protein using a structure prediction neural network to generate an intermediate output of the structure prediction neural network, wherein the structure prediction neural network is configured to process a representation of an input amino acid sequence to generate an output characterizing a predicted structure of a protein specified by the input amino acid sequence; and processing the intermediate output of the structure prediction neural network using a stability prediction neural network to generate a predicted structural stability score characterizing the predicted structural stability of the protein specified by the amino acid sequence.

20 Claims, 5 Drawing Sheets

(56) References Cited

OTHER PUBLICATIONS

Bepler et al., "Learning Protein Sequence Embeddings Using Information from Structure," 2019 (Published as a conference paper at ICLR2019), International Conference on Learning Representations, pp. 1-17 (Year: 2019).
Alipanahi, B.; Delong, A.; Weirauch, M.T.; Frey, B.J. Predicting the sequence specificities of DNA- and RNA-binding proteins by deep learning. Nat. Biotechnol. 2015, 33, 831-838 (Year: 2015).
Kuroda et al., "Antibody affinity maturation by computational design," Antibody Engineering: Methods and Protocols, 2018:15-34.
Mamoshina et al., "Applications of deep learning in biomedicine," Molecular pharmaceutics, Mar. 23, 2016, 13.5:1445-1454.
Sazli et al., "A brief review of feed-forward neural networks," Communications Faculty of Sciences University of Ankara Series, 2006, A2-A3 Physical Sciences and Engineering, 50.01:11-17.
Office Action in Chinese Appln. No. 202180067160.6, mailed on Dec. 22, 2025, 15 pages (with English translation).

* cited by examiner

PROTEIN STABILITY PREDICTION SYSTEM 100

PROTEIN DESIGN SYSTEM 300

PREDICTING PROTEIN STRUCTURAL STABILITY USING INTERMEDIATE OUTPUTS OF A PROTEIN STRUCTURE PREDICTION NEURAL NETWORK

CROSS-REFERENCE TO RELATED APPLICATION

This application claims priority under 35 U.S.C. 119 to Provisional Application No. 63/082,313, filed Sep. 23, 2020, which is incorporated by reference.

BACKGROUND

This specification relates to predicting protein structural stability.

A protein is specified by one or more sequences of amino acids. An amino acid is an organic compound which includes an amino functional group and a carboxyl functional group, as well as a side-chain (i.e., group of atoms) that is specific to the amino acid. Protein folding refers to a physical process by which a sequence of amino acids folds into a three-dimensional (3-D) configuration. The structure of a protein defines the 3-D configuration of the atoms in the amino acid sequence of the protein after the protein undergoes protein folding. When in a sequence linked by peptide bonds, the amino acids may be referred to as amino acid residues.

Predictions can be made using machine learning models. Machine learning models receive an input and generate an output, e.g., a predicted output, based on the received input. Some machine learning models are parametric models and generate the output based on the received input and on values of the parameters of the model. Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes a system implemented as computer programs on one or more computers in one or more locations for using a stability prediction neural network to predict protein structural stability and to perform protein design.

As used throughout this specification, the term "protein" may be understood to refer to any biological molecule that is specified by one or more sequences of amino acids. For example, the term protein may be understood to refer to a protein domain (i.e., a portion of an amino acid sequence that can undergo protein folding nearly independently of the rest of the amino acid sequence) or a protein complex (i.e., that is specified by multiple associated amino acid sequences).

According to a first aspect there is provided a method performed by one or more data processing apparatus for predicting structural stability of a protein specified by an amino acid sequence, the method comprising: processing an input comprising a representation of the amino acid sequence of the protein using a structure prediction neural network, in accordance with current values of structure prediction neural network parameters, to generate an intermediate output of the structure prediction neural network, wherein the structure prediction neural network is configured to process a representation of an input amino acid sequence to generate an output characterizing a predicted structure of a protein specified by the input amino acid sequence, wherein the intermediate output of the structure prediction neural network comprises an output generated by one or more hidden layers of the structure prediction neural network; and processing the intermediate output of the structure prediction neural network using a stability prediction neural network, in accordance with current values of stability prediction neural network parameters, to generate a predicted structural stability score characterizing the predicted structural stability of the protein specified by the amino acid sequence.

In some implementations, the method further comprises: determining an error between: (i) the predicted structural stability score characterizing the predicted structural stability of the protein, and (ii) a target structural stability score characterizing an actual structural stability of the protein; determining gradients of the error with respect to the current values of the stability prediction neural network parameters; and updating the current values of the stability prediction neural network parameters using the gradients in particular by backpropagation of the gradients through the stability prediction neural network.

In some implementations, the method further comprises: determining gradients of the error with respect to the current values of the structure prediction neural network parameters; and updating the current values of the structure prediction neural network parameters using the gradients, in particular by backpropagation of the gradients through the structure prediction neural network.

In some implementations, the method further comprises: determining gradients of the predicted structural stability score with respect to the representation of the amino acid sequence; and using the gradients of the predicted structure stability score with respect to the representation of the amino acid sequence to update the amino acid sequence, for example by backpropagation of the gradients through the structure prediction neural network while treating the parameter values of the structure prediction neural network as constants.

In some implementations, determining gradients of the predicted structural stability score with respect to the representation of the amino acid sequence comprises backpropagating gradients of the predicted structural stability score through both the stability prediction neural network and the structure prediction neural network.

In some implementations, using the gradients of the predicted structural stability score with respect to the representation of the amino acid sequence to update the amino acid sequence comprises updating the amino acid sequence to encourage an increase in a structural stability of the protein specified by the amino acid sequence.

In some implementations, using the gradients of the predicted structural stability score with respect to the representation of the amino acid sequence to update the amino acid sequence comprises updating the amino acid sequence to encourage a decrease in a structural stability of the protein specified by the amino acid sequence.

In some implementations, using the gradients of the predicted structural stability score with respect to the representation of the amino acid sequence to update the amino acid sequence comprises updating the amino acid sequence to encourage a structural stability of the protein specified by the amino acid sequence to match a target structural stability.

The method may further comprise making the protein specified by the amino acid sequence, e.g. the amino acid sequence that has been updated as described above. The manufactured protein may be a drug.

In some implementations, the method further comprises: determining, based at least in part on the predicted structural stability score, that the protein specified by the amino acid sequence satisfies a design criterion; and providing an output that specifies the amino acid sequence. That is, in implementations the design criterion at least specifies a target structural stability of the protein. Again, the method may include making the protein specified by the amino acid sequence; and the manufactured protein may be a drug.

In some implementations, the intermediate output of the structure prediction neural network comprises features characterizing the amino acid sequence of the protein, in particular features used by the structure prediction neural network for predicting the structure of the protein.

In some implementations, the input comprising the representation of the amino acid sequence of the protein comprises a respective embedding of an amino acid in each position of the amino acid sequence.

In some implementations of a method as described above the method is used for predicting the structural stability of the physical protein molecule. Thus the method may include determining the amino acid sequence of the physical protein molecule, and then using the method to predict the structural stability of the physical protein molecule specified by the determined amino acid sequence, in particular by generating the predicted structural stability score for the physical protein molecule, where the predicted structural stability score predicts the structural stability of the physical protein molecule.

In some implementations of a method as described above the method is used for selecting a protein for use as a drug. Such a method may comprise processing an amino acid sequence of each of a set of candidate drug proteins using the method to determine a respective predicted structural stability score for each candidate protein, and selecting one of the candidate proteins for use as the drug using the predicted structural stability score for each candidate drug protein. For example a candidate drug protein which is predicted to be most stable may be selected as the drug. However in some circumstances it may be desirable to select according to predicted stability without selecting the most stable e.g. to select a drug which, because of its lower structural stability, has a relatively shorter lifetime or which may be cleared quickly.

According to another aspect there is provided a system comprising: one or more computers; and one or more storage devices communicatively coupled to the one or more computers, wherein the one or more storage devices store instructions that, when executed by the one or more computers, cause the one or more computers to perform operations to implement the techniques described herein. The system may include a subsystem, e.g. a robotic protein synthesis subsystem, to make the protein specified by the amino acid sequence.

According to another aspect there are provided one or more non-transitory computer storage media storing instructions that when executed by one or more computers cause the one or more computers to perform operations to implement the techniques described herein.

Particular embodiments of the subject matter described in this specification can be implemented so as to realize one or more of the following advantages.

This specification describes a system for predicting structural stability of proteins. To predict the structural stability of a protein, the system processes a representation of the amino acid sequence of the protein using a structure prediction neural network (i.e., that is trained to predict the structure of the protein) to generate an intermediate output of the structure prediction neural network. The intermediate output of the structure prediction neural network provides an effective representation of the amino acid sequence that implicitly characterizes features of the amino acid sequence that are relevant to predicting the stability of the corresponding protein. The system processes the intermediate output of the structure prediction neural network using a stability prediction neural network to predict the structural stability of the protein.

Accurately predicting protein stability is a difficult problem. Processing intermediate outputs of the structure prediction neural network (rather than, e.g., raw representations of amino acid sequences) may enable the stability prediction neural network to predict protein structural stability more accurately than would otherwise be possible. For example, processing intermediate outputs of the structure prediction neural network rather than raw representations of amino acid sequences may reduce the likelihood of the stability prediction neural network over-fitting the training data used during training. Moreover, by reducing the likelihood of over-fitting, the system may enable the stability prediction neural network to be trained to achieve an acceptable level of performance using less training data, over fewer training iterations, or both, thereby reducing consumption of computational resources during training. Computational resources may include, e.g., memory and computing power.

This specification describes systems that use a stability prediction neural network to perform protein design, in particular, by identifying amino acid sequences that specify proteins having desired structural stability attributes, e.g., high structural stability, optionally as well as other desired attributes, e.g., low likelihoods of causing adverse medical reactions. For example, a protein design system may use a stability prediction neural network to iteratively update an amino acid sequence to encourage the protein specified by the amino acid sequence to achieve desired structural stability attributes. As another example, the clinical use of a potentially beneficial therapeutic protein may be limited by its lack of stability, and the techniques described herein may be used to identify a more stable, mutated version which is nonetheless therapeutically effective. Proteins that are designed using the stability prediction neural network can be used, e.g., as drugs to be administered to patients to achieve therapeutic effects, or as enzymes to catalyze industrial processes. The described methods can identify e.g. relatively more stable variants of proteins which are better for manufacture, handling, and storage.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
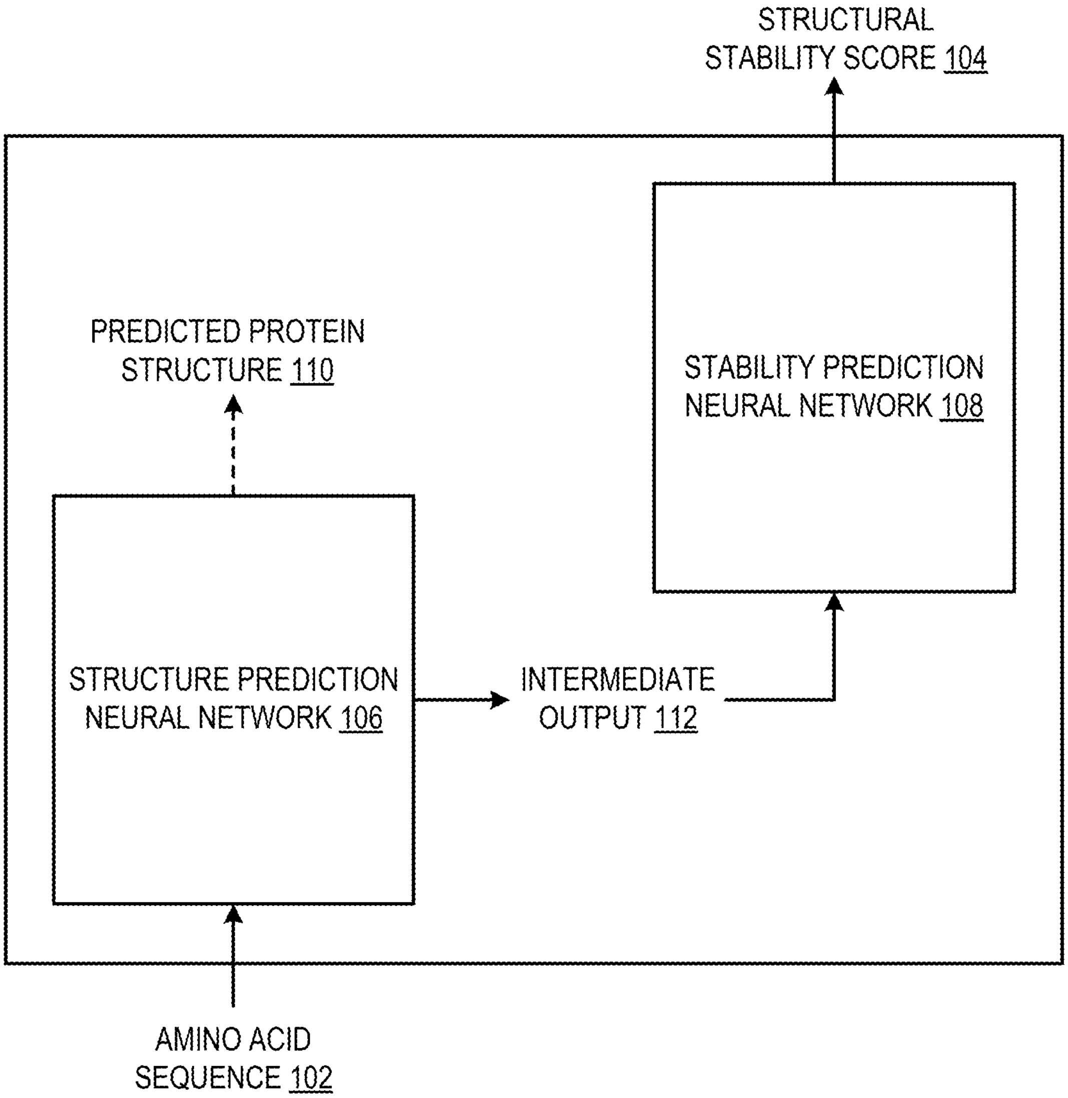
FIG. 1 shows an example protein stability prediction system.

FIG. 1 shows an example protein stability prediction system 100. The protein stability prediction system 100 is an example of a system implemented as computer programs on one or more computers in one or more locations in which the systems, components, and techniques described below are implemented.

The system 100 is configured to process data defining an amino acid sequence 102 to generate a structural stability score 104 that characterizes a predicted structural stability of the protein specified by the amino acid sequence 102.

The structural stability of a protein may refer to the likelihood that the protein will maintain its folded structure rather than reverting to its denatured (i.e., unfolded) state, or more generally to the likelihood of a change in its physical structure. In some cases, the structural stability of a protein may refer more specifically to, e.g., the thermal stability of the protein (i.e., the likelihood that the protein will maintain its folded structure at elevated temperatures), or proteolytic stability of the protein (i.e., the likelihood that the protein will maintain its folded structure in the presence of proteolytic enzymes that catalyze the breakdown of proteins).

The structural stability score 104 may be represented as a numerical value, e.g., such that a higher value of the structural stability score 104 may indicate higher stability, and a lower value of the structural stability score 104 may indicate a lower stability.

The system 100 includes a structure prediction neural network 106 and a stability prediction neural network 108, which are each described in more detail next.

Figure 2:
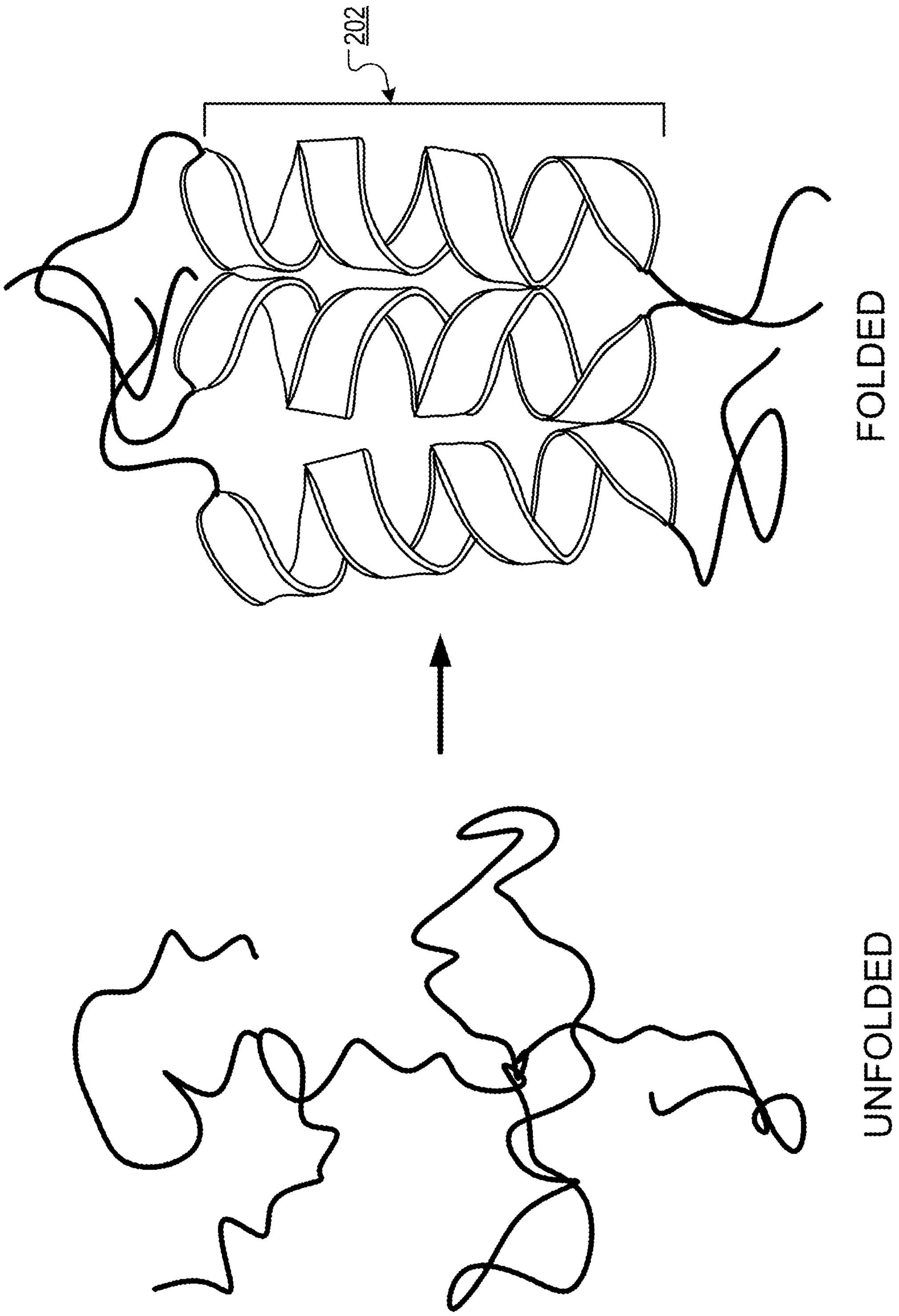
FIG. 2 is an illustration of an unfolded protein and a folded protein.

The structure prediction neural network 106 is configured to process a representation of the amino acid sequence 102 to generate an output that characterizes the predicted structure 110 of the protein specified by the amino acid sequence 102. The structure of a protein refers to the three-dimensional (3-D) configuration of the atoms in the protein after the protein undergoes protein folding. FIG. 2 provides an illustration of an unfolded protein and a folded protein.

In some implementations, the structure prediction neural network 106 may generate a set of structure parameters that define the predicted structure 110 of the protein specified by the amino acid sequence 102 e.g. in terms of a sequence of backbone atomic coordinates and/or backbone atom torsion angles of the amino acid residues. For example, the structure parameters may be a sequence of three-dimensional (3D) numerical coordinates (e.g., represented as 3D vectors) where each coordinate represents the position (in some given frame of reference) of a corresponding atom in an amino acid of the protein. In a particular example, the structure parameters may be a sequence of 3D numerical coordinates representing the respective positions of the alpha carbon atoms in the amino acids in the protein. An alpha carbon atom, which may be referred to in this specification as a backbone atom, refers to a carbon atom in an amino acid to which the amino functional group, the carboxyl functional group, and the side-chain are bonded. In another example, the structure parameters may be a sequence of torsion (i.e., dihedral) angles between specific atoms in the amino acids of the protein. For example, the structure parameters may be a sequence of phi ($\phi$), psi ($\psi$), and omega ($\omega$) dihedral angles between the backbone atoms in amino acids of the protein.

In some implementations, the structure prediction neural network 106 may generate a "distance map" that characterizes the predicted structure of the protein in terms of a respective estimated distance (e.g., measured in angstroms) between each pair of amino acids in the protein specified by the amino acid sequence 102. In some examples, a distance map may represent the estimated distance between a pair of amino acids as a binary variable, e.g., that assumes value 1 if the distance between the pair of amino acids is estimated to be less than a threshold value (e.g., 8 Angstroms), and 0 otherwise. In some examples, a distance map may represent the estimated distance between a pair of amino acids as a probability distribution over a set of possible distances. A distance map may be represented as an ordered collection of numerical values, e.g., a vector or matrix of numerical values.

To generate an output characterizing the predicted protein structure 110, the structure prediction neural network 106 processes an input that includes a representation of the amino acid sequence 102. The representation of the amino acid sequence may include a respective embedding (i.e., an ordered collection of numerical values, e.g., a vector or matrix of numerical values) corresponding to each position in the amino acid sequence. The respective embedding corresponding to each position in the amino acid sequence 102 may comprise, e.g., a one-hot vector that defines the identity of the amino acid in the position in the amino acid sequence 102. A one-hot vector has a different component corresponding to each possible amino acid (e.g., of a predetermined number of possible amino acids). A one-hot vector representing a particular amino acid has value one (or some other predetermined value) in the component corresponding to the particular amino acid and value zero (or some other predetermined value) in the other components.

Optionally, the structure prediction neural network 106 may process other inputs in addition to the representation of the amino acid sequence 102. For example, the structure prediction neural network 106 may process a representation of a multiple sequence alignment (MSA) corresponding to the amino acid sequence 102. The MSA may specify a sequence alignment of the amino acid sequence 102 with multiple additional amino acid sequences, e.g., from other proteins. An MSA may be generated, e.g., by processing a database of amino acid sequences using any appropriate computational sequence alignment technique, e.g., progressive alignment construction. The amino acid sequences in the MSA may be understood as having an evolutionary relationship, e.g., where each amino acid sequence in the MSA may share a common ancestor. The correlations between the amino acid sequences in the MSA may encode information that is relevant to predicting the structure of the protein. The MSA may use the same one-hot encoding as the amino acid sequence 102 with an additional category for an insertion (or deletion) of an amino acid residue.

As part of generating the predicted protein structure 110, the structure prediction neural network 106 generates an intermediate output 112. Generally, an intermediate output 112 of a neural network refers to an output generated by one or more hidden layers of the neural network, i.e., layers other than the output layer that generates the predicted protein structure 110. The intermediate output 112 may be represented as an ordered collection of numerical values, e.g., a vector or matrix of numerical values. In one example, the intermediate output 112 may be an output generated by a fully-connected, convolutional, or self-attention hidden neural network layer of the structure prediction neural network 106, and may include a respective embedding (e.g., vector) corresponding to each position in the amino acid sequence 102.

The stability prediction neural network 108 is configured to process the intermediate output 112 generated by the structure prediction neural network 106 to generate the structural stability score 104. The intermediate output 112 implicitly characterizes features of the amino acid sequence 102, in particular, features of the amino acid sequence 102 that are relevant to predicting the stability of the protein specified by the amino acid sequence 102. That is, the intermediate output 112 provides an effective representation of the amino acid sequence 102 that the stability prediction neural network 108 processes to generate the structural stability score 104.

Optionally, the stability prediction neural network 108 may process other inputs in addition to the intermediate output 112 of the structure prediction neural network 106. For example, the stability prediction neural network 108 may additionally process a representation of the predicted protein structure 110 of the protein specified by the amino acid sequence 102, a representation of an MSA corresponding to the amino acid sequence 102, or both.

In some implementations, the stability prediction neural network 108 is configured to process the intermediate output 112 but not the predicted protein structure 110. In these implementations, the structure prediction neural network 106 may perform only those operations necessary to generate the intermediate output 112, and in particular, the structure prediction neural network 106 may refrain from performing all the operations necessary to generate the predicted protein structure 110. The structure prediction neural network 106 may refrain from performing all the operations necessary to generate the predicted protein structure 110, e.g., to reduce unnecessary use of computational resources.

The system 100 may train the stability prediction neural network 108 on a set of training examples that each include: (i) a training amino acid sequence, and (ii) a target structural stability score, i.e., that represents the actual structural stability of the protein specified by the training amino acid sequence. The target structural stability score may be determined, e.g., by physical (laboratory) experiments such as differential scanning calorimetry, circular dichroism, and other methods. There is a substantial body of experimental work characterizing protein stability and databases of experimentally determined structural stability scores are available. Any suitable measure of structural stability may be employed for the target structural stability score, such as (but not limited to) a change in free energy between folded and unfolded states (ΔΔG) or a thermal stability measure such as a melt temperature (Tm).

The system 100 may train the stability prediction neural network using an appropriate machine learning training technique, e.g., stochastic gradient descent. More specifically, at each of one or more training iterations, the system 100 may generate predicted structural stability scores 104 for each of one or more training amino acid sequences (e.g., that are randomly sampled from the set of training amino acid sequences). The system 100 may determine a respective error (e.g., a squared-error) between each predicted structural stability score 104 and the corresponding target structural stability score, and then determine gradients of the errors with respect to the current values of a set of parameters of the stability prediction neural network. The system may determine the gradients of the errors with respect to the current values of the stability prediction neural network parameters, e.g., using backpropagation.

The system 100 may use the gradients to adjust the current values of the stability prediction neural network parameters using a gradient descent optimization technique (e.g., RMSprop) to encourage the stability prediction neural network 108 to generate predicted structural stability scores that match the target structural stability scores. That is, the system 100 may backpropagate gradients of the errors through the stability prediction neural network to adjust the current values of the stability prediction neural network parameters.

Optionally, the system 100 may jointly train the structure prediction neural network 106 along with the stability prediction neural network 108. More specifically, at each training iteration, the system 100 may determine gradients of the errors with respect to the current values of both: (i) the set of stability prediction neural network parameters, and (ii) a set of parameters of the structure prediction neural network. In particular, the system 100 may determine gradients of the errors with respect to a (proper) subset of the structure prediction neural network parameters that are involved in generating the intermediate outputs 112 provided to the stability prediction neural network. That is, the system 100 may backpropagate gradients of the errors through the stability prediction neural network 108 and into the structure prediction neural network 106 to update the current parameter values of both neural networks. Jointly training the structure prediction neural network 106 along with the stability prediction neural network 108 may improve the performance (e.g., prediction accuracy) of the structure prediction neural network 106, e.g., by encouraging the structure prediction neural network 106 to generate more informative internal feature representations of amino acid sequences.

Alternatively to or in combination with the joint training described above, the system 100 may train the structure prediction neural network 106 on a set of training examples that each include: (i) a training amino acid sequence, and (ii) a target protein structure. The target protein structure may represent the actual structure of the protein specified by the training amino acid sequence and may be determined, e.g., by physical (laboratory) experiments, e.g., x-ray crystallography or cryo-electron microscopy. The system 100 may train the structure prediction neural network 106 on the training examples using an appropriate machine learning training technique, e.g., stochastic gradient descent.

Generally, the stability prediction neural network 108 and the structure prediction neural network 106 may have any appropriate neural network architectures that enable them to perform their described functions. More specifically, the neural networks may have respective architectures that include any appropriate types of neural network layers (e.g., fully-connected layers, convolutional layers, pooling layers, self-attention layers, etc.), arranged in any appropriate configuration (e.g., as a linear sequence of layers).

Structural stability scores 104 generated by the stability prediction neural network 108 can be used for any of a variety of purposes. For example, the structural stability scores can be used to facilitate protein design, i.e., determining an amino acid sequence that specifies a protein which is predicted to satisfy one or more protein design criteria, e.g., that specify a target structural stability of the protein. Examples of protein design systems that use the stability prediction neural network 108 are described in more detail with reference to FIG. 3 and FIG. 4.

FIG. 2 is an illustration of an unfolded protein and a folded protein. The unfolded protein is a random coil of amino acids. The unfolded protein undergoes protein folding and folds into a 3D configuration. Protein structures often include stable local folding patterns such alpha helices (e.g., as depicted by 202) and beta sheets.

Figure 3:
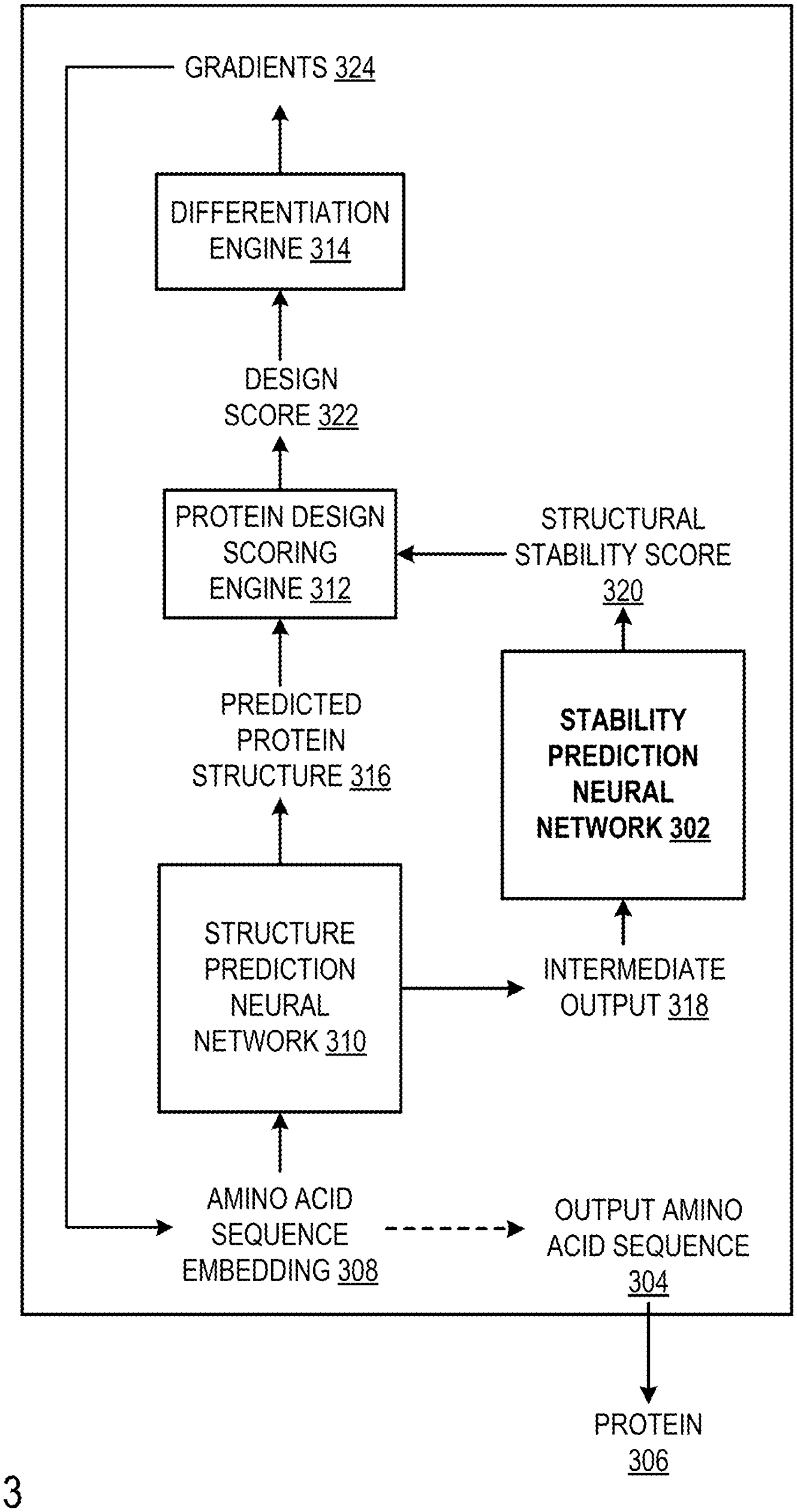
FIG. 3 shows an example protein design system that uses a stability prediction neural network.

FIG. 3 shows an example protein design system 300 that uses a stability prediction neural network. The protein design system 300 is an example of a system implemented as computer programs on one or more computers in one or more locations in which the systems, components, and techniques described below are implemented.

The system 300 uses a stability prediction neural network 302 to determine an "output" amino acid sequence 304 that specifies a protein 306 which is predicted to satisfy one or more protein design criteria. The design criteria specify one or more desired attributes of the protein 306, e.g., the design criteria may specify a target structural stability of the protein 306 e.g. as a target structural stability score. The design criteria may be provided to the system 300 by a user of the system 300, e.g., through an interface made available by the system 300. The user may be a remote user that provides the design criteria to the system 300 over a communications network, e.g., the internet.

To determine the output amino acid sequence 304, the system 300 maintains and iteratively updates an amino acid sequence embedding 308 representing an amino acid sequence over a sequence of optimization iterations. As used throughout this specification, an "embedding" of an entity (e.g., an amino acid or an amino acid sequence) refers to an ordered collection of numerical values, e.g., a vector or matrix of numerical values, which represents the entity. The amino acid sequence embedding 308 may include a respective embedding corresponding to each position in the amino acid sequence, i.e., where the embedding corresponding to a position in the amino acid sequence represents the identity of the amino acid at the position in the amino acid sequence. The system 300 iteratively updates the amino acid sequence embedding 308 to encourage the protein specified by the amino acid sequence embedding 308 to satisfy the design criteria.

To initialize the amino acid sequence embedding 308 prior to the first optimization iteration, the system 300 may determine an initial amino acid sequence, e.g., by randomly sampling the identity of the amino acid in each position of the initial amino acid sequence from a set of possible amino acids. The set of possible amino acids may include, e.g., alanine, arginine, asparagine, etc, e.g. the set of "standard" amino acids. The system 300 may randomly sample the length of the initial amino acid sequence from a range of possible lengths, e.g., the integer values in the range [50, 1000]. The "length" of an amino acid sequence may refer to the number of positions in the amino acid sequence.

After determining the initial amino acid sequence, the system 300 may initialize the amino acid sequence embedding 308 as an embedding of the initial amino acid sequence. The system 300 may determine an embedding of the initial amino acid sequence, e.g., by concatenating a respective embedding corresponding to each position in the initial amino acid sequence. The system 300 may determine the respective embedding corresponding to each position in the initial amino acid sequence to be a predefined embedding, e.g., a one-hot embedding, of the amino acid at the position in the initial amino acid sequence. A one-hot embedding of a given amino acid has a different component corresponding to each possible amino acid (e.g., of a predetermined number of possible amino acids), where the component corresponding to the given amino acid has value one (or some other predetermined value), and each other component has value zero (or some other predetermined value).

The system 300 uses a structure prediction neural network 310, a stability prediction neural network 302, a protein design scoring engine 312, and a differentiation engine 314, which will each be described in more detail next, to iteratively update the amino acid sequence embedding 308 over multiple optimization iterations.

At each optimization iteration, the structure prediction neural network 310 processes an input that includes the current amino acid sequence embedding 308 to generate an output characterizing the predicted structure 316 of the protein specified by the current amino acid sequence embedding 308 (i.e., the "current protein"). The predicted structure 316 may characterize an estimated 3-D configuration of the atoms in the current protein after it undergoes protein folding. As part of generating the predicted structure 316, the structure prediction neural network 310 also generates an intermediate output 318, as described above with reference to FIG. 1.

At each optimization iteration, the stability prediction neural network 302 processes the intermediate output 318 of the structure prediction neural network 310 to generate a structural stability score 320 that characterizes a predicted structural stability of the current protein, as described above with reference to FIG. 1.

At each optimization iteration, the protein design scoring engine 312 determines a design score 322 that characterizes how well the current protein specified by the amino acid sequence embedding 308 satisfies the design criteria. The scoring engine 312 determines the design score 322 based at least in part on the structural stability score 320 for the current protein, and optionally on other data characterizing the current protein, e.g., the predicted structure 316 of the current protein. Generally, the design criteria specify one or more desired attributes of the protein 306 specified by the output amino acid sequence 304. The scoring engine 312 may determine a respective score for each attribute specified by the design criteria that characterizes whether (or the degree to which) the current protein possesses the attribute. The scoring engine 312 may determine the design score 322 as a function, e.g., a weighted linear combination, of the attribute scores. A few examples of attributes scores are described in more detail next.

In one example, one of the attributes specified by the design criteria may be that the protein 306 specified by the output amino acid sequence 304 should have a desired structural stability. In some examples, the desired structural stability may be defined by a target structural stability score. In these examples, the scoring engine 312 may determine the score for this attribute as an error (e.g., a squared error) between: (i) the predicted structural stability score 320 generated by the stability prediction neural network 302, and (ii) the target structural stability score. In some examples, the desired structural stability may be the highest possible stability that can be achieved in conjunction with satisfying the other design criteria, and the scoring engine 312 may determine the score for this attribute to be equal to the predicted structural stability score 320.

In another example, one of the attributes specified by the design criteria may be that the protein 306 specified by the output amino acid sequence 304 should have a "goal" (i.e., target) protein structure. The scoring engine 312 may determine the score for this attribute (a structure score) that characterizes a similarity between: (i) the predicted structure 316 of the current protein, and (ii) the goal protein structure.

The goal protein structure may be specified by a set of goal structure parameters, e.g., that include a sequence of dihedral angles between the backbone atoms in amino acids in the goal protein structure and/or a sequence of backbone atomic coordinates. The scoring engine 312 may determine the structure score based on a similarity measure between: (i) the predicted structure 316 of the current protein, and (ii) the goal protein structure. In one example, the similarity measure may be a root-mean-square-deviation (RMSD) between the structure parameters defining the predicted structure 316 and structure parameters defining the goal protein structure.

In another example, one of the attributes specified by the design criteria may be that the protein 306 specified by the output amino acid sequence 304 should bind selectively and specifically to a "binding target" (or "ligand"). The binding target may be, e.g., an ion (e.g., aluminum—Al 3+), a small molecule (e.g., adenosine triphosphate-ATP), or a macromolecule (e.g., another protein or a lipid). In this example, the scoring engine 312 may determine the score for this attribute (a binding (affinity) score) that characterizes the predicted strength of the binding interaction between: (i) the current protein specified by the current amino acid sequence embedding 308, and (ii) the binding target.

In another example, one of the attributes specified by the design criteria may be that the protein 306 specified by the output amino acid sequence 304 should have a low likelihood of being associated with an adverse medical reaction, e.g., an allergic reaction, nerve injury, organ injury, or impaired vision or hearing. In this example, the scoring engine 312 may determine the score for this attribute (an adverse reaction score) based at least in part on a predicted likelihood that the current protein having the predicted structure 316 is associated with an adverse medical reaction, e.g. based upon existing databases reporting adverse drug reactions.

The scoring engine 312 may determine certain attribute scores, e.g., binding scores and adverse reaction scores, using an attribute prediction neural network that is trained to generate the attribute score (e.g., the stability prediction neural network 302 may be a particular example of an attribute prediction neural network). The attribute prediction neural network may process an input that includes, e.g., the predicted protein structure 316, the amino acid sequence embedding 308, intermediate outputs of the structure prediction neural network 310, or a combination thereof. The attribute prediction neural network may be trained on a set of training examples that each specify: (i) a respective training input that includes data characterizing a protein structure and/or an amino acid sequence, and (ii) a target attribute score that should be generated by the attribute prediction neural network by processing the training input. The target attribute score may be, e.g., a binding score or an adverse reaction score. The target attribute scores may be determined, e.g., by physical experiments, or in silico, or from published experimental data e.g. in relevant databases. The attribute prediction neural network may be trained using an appropriate training technique, e.g., stochastic gradient descent, to minimize an error between: (i) predicted attribute scores generated by the attribute prediction neural network, and (ii) target attribute scores specified by the training examples. The attribute prediction neural network may have any appropriate neural network architecture that enables it to perform its described function, e.g., an architecture that includes one or more fully-connected neural network layers, convolutional neural network layers, pooling neural network layers, self-attention neural network layers, or a combination thereof.

In a particular example, the scoring engine 312 may use an attribute prediction neural network to generate the binding score between: (i) the current protein, and (ii) a binding target that includes a target protein, using a binding prediction neural network. The binding prediction neural network may be configured to process respective representations of: (i) the predicted structure 316 of the current protein, and (ii) the (predicted) structure of the target protein, to generate the binding score for the current protein and the target protein.

At each optimization iteration, the differentiation engine 314 determines gradients 324 (i.e., first derivatives) of the design score 322 with respect to the current amino acid sequence embedding 308. More specifically, the differentiation engine 314 determines a respective gradient of the design score 322 with respect to each component of the current amino acid sequence embedding. As mentioned above, in implementations the design score 322 is dependent upon at least the structural stability score 320. The differentiation engine 314 can use any appropriate computational methods to determine the gradients of the design score 322 with respect to the current amino acid sequence embedding 308, e.g., automatic differentiation methods (e.g., backpropagation), numerical differentiation methods (e.g., finite difference methods), analytic differentiation methods, or a combination thereof.

Generally, the design score 322 may be expressed as a function (e.g., a weighted linear combination) of one or more attribute scores (as described above). One or more of the attribute scores may be functions of the predicted structure 316 generated by the structure prediction neural network 310 or of an intermediate output 318 generated by the structure prediction neural network 310. To determine the gradients 324 of the design score 322 with respect to the amino acid sequence embedding 308, the differentiation engine 314 may use a variation of the backpropagation algorithm that is typically used to determine gradients with respect to the current parameter values of a neural network. More specifically, the differentiation engine 314 may treat the parameter values of the structure prediction neural network 310 as constants and use backpropagation to determine gradients 324 of the design score 322 with respect to the amino acid sequence embedding 308. That is, the differentiation engine 314 may backpropagate gradients of the design score 322 through the structure prediction neural network, while treating the parameter values of the structure prediction neural network as constants, to determine gradients 324 of the design score with respect to the amino acid sequence embedding 308.

The design score 322 is based at least in part on the structural stability score 320 generated by the stability prediction neural network 302. Therefore, as part of determining gradients of the design score 322 with respect to the amino acid sequence embedding 308, the differentiation engine 314 determines gradients 324 of the predicted structural stability score 320 with respect to the amino acid sequence embedding 308. To this end, the differentiation engine 314 may treat the parameter values of both the stability prediction neural network 302 and the structure prediction neural network 310 as constants and use backpropagation to determine gradients of the predicted structural stability score 320 with respect to the amino acid sequence embedding. That is, the differentiation engine 314 may backpropagate gradients of the structural stability score 320 through the both the stability prediction neural network 302 and the structure prediction neural network 310 to determine gradients of the structural stability score 320 with respect to the amino acid sequence embedding 308.

More generally, one or more of the attribute scores (i.e., that are used to compute the design score 322) may be generated by processing the predicted structure 316 or an intermediate output 318 generated by the structure prediction neural network 310 using a respective attribute prediction neural network. In these implementations, to determine the gradients 324 of the design score 322 with respect to the amino acid sequence embedding 308, the differentiation engine 314 may backpropagate gradients of the attribute scores through both the attribute prediction neural networks and the structure prediction neural network 310.

At each optimization iteration, the system 300 uses the gradients 324 of the design score 322 with respect to the amino acid sequence embedding 308 (i.e., including the gradients 324 of the structural stability score 320) to update the amino acid sequence embedding 308. The system may update the amino acid sequence embedding 308 to optimize the design score 322, i.e., such that updated amino acid sequence embedding may be associated with a superior (e.g., higher) design score 322 than the original amino acid sequence embedding. In particular, the system 300 may update the amino acid sequence embedding 308 to encourage an increase or decrease in the structural stability of the protein, or to encourage the structural stability of the protein to match a target structural stability (e.g., defined by a target structural stability score).

The system 300 can update the amino acid sequence embedding 308 using the gradients 324 based on the update rule from any appropriate gradient descent optimization algorithm, for example, Adam, RMSprop, Adagrad, Adadelta, and AdaMax, amongst others. In some cases, the system 300 can update the amino acid sequence embedding 308 using the gradients 324 of the design score 322 based on a "warm" gradient descent update rule that includes "momentum". When the update rule includes momentum, the update to the amino acid sequence embedding 308 at the current optimization iteration may be determined based in part on the update to the amino acid sequence embedding 308 at the previous optimization iteration. An example of a warm gradient descent update rule that includes momentum is described with reference to: R. M. Neal, "MCMC using Hamiltonian dynamics", Ch. 5, Handbook of Markov Chain Monte Carlo, Chapman & Hall/CRC Press, 2011. In this manner, the system 300 can enable the amino acid sequence embedding to "roll around" the design score surface during optimization rather than directly finding a local minimum of the design score surface. The design score surface refers to the high-dimensional surface defined by the mapping from amino acid sequence embeddings to design scores.

After updating the amino acid sequence embedding 308 using the gradients of the design score, the system 300 may replace the respective embedding corresponding to each position in the amino acid sequence by a respective one-hot embedding representing the identity of an amino acid. For example, for each position in the amino acid sequence, the system 300 may identify a respective score corresponding to each possible amino acid as the value of the corresponding component of the embedding for the position in the amino acid sequence. The system 300 may then use the scores to identify an amino acid for the position, and replace the embedding for the position by a one-hot embedding representing the amino acid. In one example, the system 300 may identify the amino acid for the position as the possible amino acid having the highest score. In another example, the system 300 may identify the amino acid for the position by determining a probability distribution over the set of possible amino acids, e.g., by processing the scores using a soft-max function, and then sampling an amino acid in accordance with the probability distribution.

The system 300 may determine that the current optimization iteration is the final optimization iteration once a termination criterion is satisfied, e.g., once a predetermined number of optimization iterations have been performed, or once the design score at the current optimization iteration achieves (e.g., exceeds) a predefined threshold.

After the final optimization iteration, the system 300 selects an amino acid sequence specified by one of the amino acid sequence embeddings generated during the optimization, i.e., at one of the optimization iterations, as the output amino acid sequence 304 specifying the protein 306. For example, the system 300 may select the amino acid sequence specified by the current amino acid sequence embedding at the final optimization iteration as the output amino acid sequence 304. As another example, the system 300 may select the amino acid sequence specified by the amino acid sequence embedding corresponding to the best (e.g., highest) design score among all the amino acid sequence embeddings generated during the optimization as the output amino acid sequence 304.

In some cases, rather than selecting a single output amino acid sequence 304, the system 300 may select multiple output amino acid sequences 304 specifying respective proteins 306. For example, the system 300 may select a predefined number of amino acid sequences specified by the amino acid sequence embeddings corresponding to the best (e.g., highest) design scores from among all the amino acid sequence embeddings generated during the optimization as respective output amino acid sequences 304.

Optionally, the system 300 may repeatedly perform the optimization procedure to generate multiple output amino acid sequences 304, each of which may be different, e.g., due to randomness in the way the amino acid sequence embedding 308 is initialized prior to the first optimization iteration.

Generally, the protein 306 specified by the output amino acid sequence 304 generated by the system 300 may not strictly satisfy some, or any, of the protein design criteria that characterized the optimization performed by the system 300. For example, if the protein design criteria specify a target structural stability score for the protein 306, the predicted structural stability score of the protein 306 may not precisely match the target structural stability score. The protein 306 may not strictly satisfy all the protein design criteria, e.g., because biochemical constraints may prevent the protein from strictly satisfying the design criteria, or because the optimization performed by the system 300 may have converged to an undesirable local optimum of the design scores.

A protein having the output amino acid sequence 304 generated by the system 300 may be experimentally synthesized and validated, e.g., to determine by physical experiments whether the synthesized protein actually achieves the design criteria provided to the system 300. The synthesis may be manual, or semi- or wholly automatic. Proteins designed by the system 300 can be used for any of a variety of practical applications, e.g., as drugs to be administered to patients to achieve therapeutic effects, or as enzymes to catalyze industrial processes.

Figure 4:
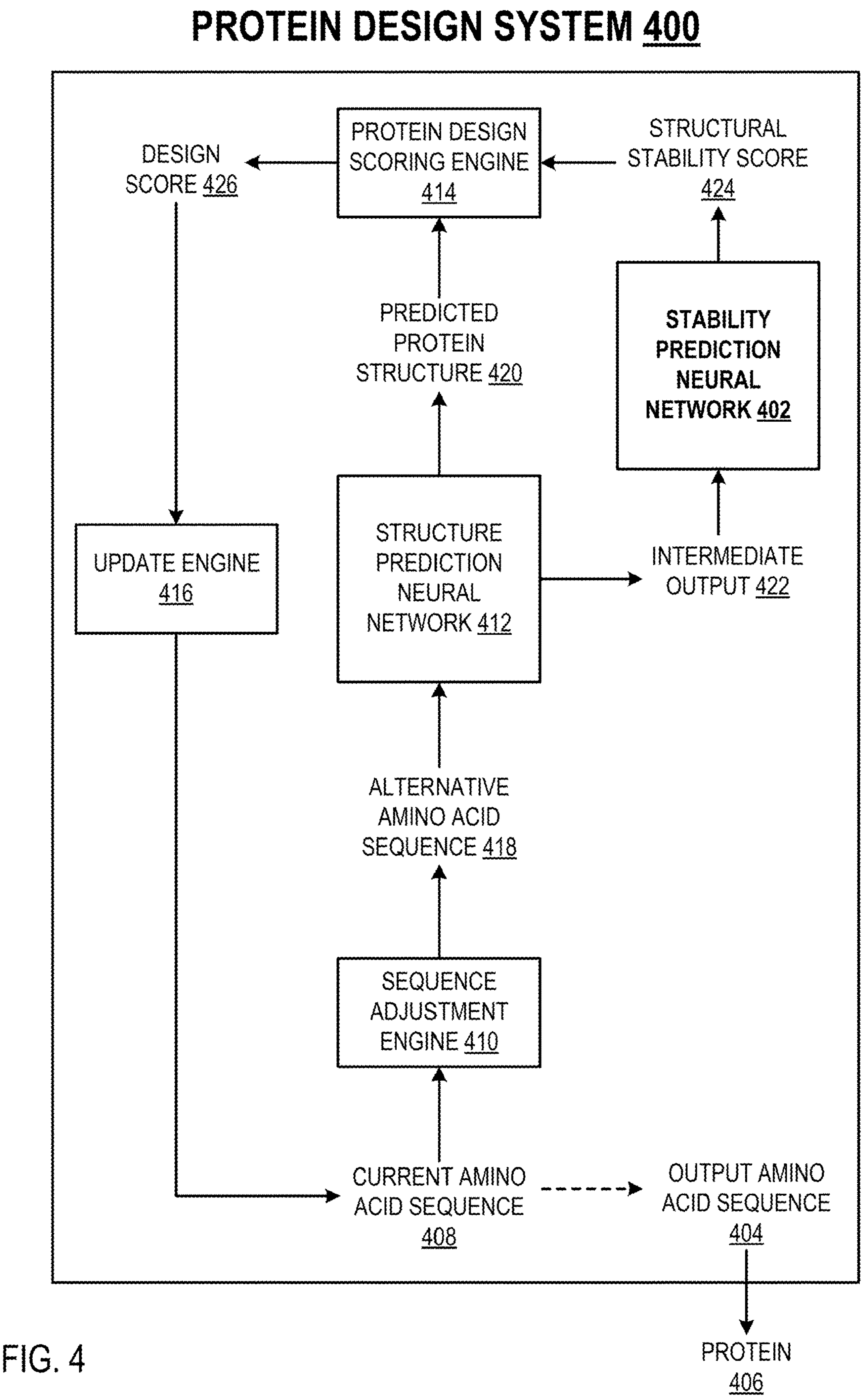
FIG. 4 shows another example protein design system that uses a stability prediction neural network.

FIG. 4 shows an example protein design system 400 that uses a stability prediction neural network. The protein design system 400 is an example of a system implemented as computer programs on one or more computers in one or more locations in which the systems, components, and techniques described below are implemented.

The system 400 uses a stability prediction neural network 402 to determine an "output" amino acid sequence 404 that specifies a protein 406 which is predicted to satisfy one or more protein design criteria. The design criteria specify one or more desired attributes of the protein 406, e.g., the design criteria may specify a target structural stability of the protein 406. The design criteria may be provided to the system 400 by a user of the system 400, e.g., through an interface made available by the system 400. The user may be a remote user that provides the design criteria to the system 400 over a communications network, e.g., the internet.

To determine the output amino acid sequence 404, the system 400 maintains and iteratively adjusts a "current" amino acid sequence 408 over a sequence of optimization iterations to encourage the protein specified by the current amino acid sequence 408 to satisfy the design criteria. Prior to the first optimization iteration, the system 400 may initialize the current amino acid sequence 408, e.g., by randomly sampling the identity of the amino acid in each position of the current amino acid sequence 408 from a set of possible amino acids. The set of possible amino acids may include, e.g., alanine, arginine, asparagine, etc, e.g. the set of "standard" amino acids. The system 400 may randomly sample the initial length of the current amino acid sequence 408 from a range of possible lengths, e.g., the integer values in the range [50, 1000]. The "length" of an amino acid sequence may refer to the number of positions in the amino acid sequence. Rather than the current amino acid sequence 408 being randomly initialized prior to the first optimization iteration, the current amino acid sequence 408 may be initialized to the amino acid sequence of a known protein, e.g., that is specified by a user of the system 400.

The system 400 uses a sequence adjustment engine 410, a structure prediction neural network 412, a stability prediction neural network 402, a protein design scoring engine 414, and an update engine 416, which will each be described in more detail next, to iteratively adjust the current amino acid sequence 408 over multiple optimization iterations.

At each optimization iteration, the sequence adjustment engine 410 processes the current amino acid sequence 408 to generate an alternative amino acid sequence 418, i.e., that is different than the current amino acid sequence 408. The sequence adjustment engine 410 can generate the alternative amino acid sequence 418 by modifying the current amino acid sequence 408 in any of a variety of ways. A few example techniques for modifying the current amino acid sequence 408 to generate the alternative amino acid sequence 418 are described in more detail next.

In one example, the sequence adjustment engine 410 may generate the alternative amino acid sequence 418 by randomly selecting a predetermined number of positions in the current amino acid sequence 408, and randomly modifying the respective identity of the amino acid at each selected position. The sequence adjustment engine 410 may randomly modify the identity of an amino acid at a position in the current amino acid sequence 408, e.g., by randomly sampling a new identity of the amino acid in accordance with a probability distribution over the set of possible amino acids. The probability distribution over the set of possible amino acids may be, e.g., a uniform probability distribution that assigns an equal likelihood to each possible amino acid. In another example, the probability distribution over the set of possible amino acids may assign a respective likelihood to each possible amino acid based on the frequency of occurrence of the possible amino acid in the amino acid sequences of proteins in a set of known proteins. In particular, the probability distribution may assign a higher likelihood to possible amino acids that occur more frequency in the amino acid sequences of proteins in the set of known proteins.

In another example, the sequence adjustment engine 410 may generate the alternative amino acid sequence 418 by increasing or decreasing the length of the current amino acid sequence 408.

To increase the length of the current amino acid sequence 408, the sequence adjustment engine 410 may add one or more new positions to the current amino acid sequence 408, e.g., at randomly selected locations within the current amino acid sequence 408. The sequence adjustment engine 410 may determine the number of new positions to be added to the current amino acid sequence 408, e.g., by randomly sampling the number of new positions to be added from a predetermined set of non-negative integer values. The sequence adjustment engine 410 may determine the respective identity of the amino acid at each new position added to the current amino acid sequence 408, e.g., by randomly sampling the identity of the amino acid in accordance with a probability distribution over a set of possible amino acids. Example techniques for randomly sampling from a set of possible amino acids are described in more detail above.

To decrease the length of the current amino acid sequence 408, the sequence adjustment engine 410 may remove one or more positions from the current amino acid sequence 408. For example, the sequence adjustment engine 410 may randomly sample the number of positions to be removed from a predetermined set of non-negative integer values, and randomly select the positions to be removed from within the current amino acid sequence 408.

Generally, the sequence adjustment engine 410 may generate the alternative amino acid sequence 418 by modifying the current amino acid sequence 408 in a combination of ways. For example, the sequence adjustment engine 410 may modify the current amino acid sequence by a combination of adding one or more new positions, removing one or more existing positions, and modifying the identities of amino acids at one or more existing positions in the current amino acid sequence.

At each optimization iteration, the structure prediction neural network 412 processes a representation of the alternative amino acid sequence 418 to generate an output that characterizes the predicted structure 420 of the protein specified by the alternative amino acid sequence 418 (i.e., the "alternative protein"). The predicted structure 420 may characterize an estimated 3-D configuration of the atoms in the alternative protein after the alternative protein undergoes protein folding, as described above with reference to FIG. 1. As part of generating the predicted structure 420, the structure prediction neural network 412 also generates an intermediate output 422, as described above with reference to FIG. 1.

At each optimization iteration, the stability prediction neural network 402 processes the intermediate output 422 of the structure prediction neural network 412 to generate a structural stability score 424 that characterizes a predicted structural stability of the alternative protein, as described above with reference to FIG. 1.

At each optimization iteration, the protein design scoring engine 414 determines a design score 426 that characterizes how well the alternative protein specified by the alternative amino acid sequence 418 satisfies the design criteria. The scoring engine 414 determines the design score 426 based at least in part on the structural stability score 424 for the alternative protein, and optionally on other data characterizing the alternative protein, e.g., the predicted structure 420 of the alternative protein. Generally, the design criteria specify one or more desired attributes of the protein 406 specified by the output amino acid sequence 404. The scoring engine 414 may determine a respective score for each attribute specified by the design criteria that characterizes whether (or the degree to which) the alternative protein possesses the attribute. The scoring engine 414 may determine the design score 426 as a function, e.g., a weighted linear combination, of the attribute scores. A few examples of attribute scores are described in more detail next.

In one example, one of the attributes specified by the design criteria may be that the protein 406 specified by the output amino acid sequence 404 should have a desired structural stability. In some examples, the desired structural stability may be defined by a target structural stability score. In these examples, the scoring engine 414 may determine the score for this attribute as an error (e.g., a squared error) between: (i) the predicted structural stability score 424 generated by the stability prediction neural network 402, and (ii) the target structural stability score. In some examples, the desired structural stability may be the highest possible stability that can be achieved in conjunction with satisfying the other design criteria, and the scoring engine 414 may determine the score for this attribute to be equal to the predicted structural stability score 424.

In another example, one of the attributes specified by the design criteria may be that the protein 406 specified by the output amino acid sequence 404 should have a "goal" (i.e., target) protein structure. The scoring engine 414 may determine the score for this attribute (a structure score) that characterizes a similarity between: (i) the predicted structure 420 of the alternative protein, and (ii) the goal protein structure.

In some implementations, the goal protein structure may be specified by a set of goal structure parameters. The goal structure parameters may include, e.g., a sequence of dihedral angles between the backbone atoms in amino acids in the goal protein structure, or respective coordinates defining the 3-D spatial positions of the backbone atoms in the goal protein structure.

In some implementations, the goal protein structure may be specified in terms of secondary protein structure elements. A secondary protein structure element defines a structure that may be assumed by a sub-sequence of the amino acid sequence of a protein, i.e., by a local segment of the protein. Examples of secondary protein structure elements include alpha helices, beta sheets, beta turns, and omega loops. The goal protein structure may be expressed in terms of secondary protein structure elements, e.g., by indicating a respective number of each of one or more secondary protein structure elements that should occur in the goal protein structure, or by indicating a sequence of respective secondary protein structure elements that should occur in the goal protein structure. In particular examples, the goal protein structure may be required to include a first number of alpha helices and a second number of beta sheets, or the goal protein structure may be required to include an alpha helix followed by a beta sheet.

The scoring engine 414 may determine the structure score based on a similarity measure between: (i) the predicted structure 420 of the alternative protein, and (ii) the goal protein structure. In one example, the similarity measure may be a root-mean-square-deviation (RMSD) between the structure parameters defining the predicted structure 420 and structure parameters defining the goal protein structure. In another example, the similarity measure may be based on how many of the secondary protein structure elements of the goal protein structure are achieved in the predicted structure of the alternative protein.

In another example, one of the attributes specified by the design criteria may be that the protein 406 specified by the output amino acid sequence 404 should bind selectively and specifically to a "binding target" (or "ligand"). The binding target may be, e.g., an ion (e.g., aluminum—Al 3+), a small molecule (e.g., adenosine triphosphate—ATP), or a macromolecule (e.g., another protein or a lipid). In this example, the scoring engine 414 may determine the score for this attribute (a binding (affinity) score) that characterizes the predicted strength of the binding interaction between: (i) the alternative protein specified by the alternative amino acid sequence 418, and (ii) the binding target.

In another example, one of the attributes specified by the design criteria may be that the protein 406 specified by the output amino acid sequence 404 should have a low likelihood of being associated with an adverse medical reaction, e.g., an allergic reaction, nerve injury, organ injury, or impaired vision or hearing. In this example, the scoring engine 414 may determine the score for this attribute (an adverse reaction score) based at least in part on a predicted likelihood that the alternative protein having the predicted structure 420 is associated with an adverse medical reaction.

The scoring engine 414 may determine certain attribute scores, e.g., the binding scores and adverse reaction scores, using an attribute prediction machine learning model that is trained to generate the attribute score (e.g., the stability prediction neural network 402 may be a particular example of an attribute prediction neural network). The attribute prediction machine learning model may process an input that includes, e.g., the predicted protein structure 420, the alternative amino acid sequence 418, intermediate outputs of the structure prediction neural network 412, or a combination thereof. The attribute prediction machine learning model may be trained on a set of training examples that each specify: (i) a respective training input that includes data characterizing a protein structure and/or an amino acid sequence, and (ii) a target attribute score that should be generated by the attribute prediction machine learning model by processing the training input. The target attribute score may be, e.g., a binding score or an adverse reaction score. The target attribute scores may be determined, e.g., by physical experiments or otherwise as previously described.

The attribute prediction machine learning model may be trained using an appropriate training technique to minimize an error between: (i) predicted attribute scores generated by the attribute prediction neural network, and (ii) target attribute scores specified by the training examples. The attribute prediction machine learning model may be, e.g., a neural network, a support vector machine, a random forest, a regression model, or any other appropriate machine learning model. An attribute prediction neural network may have any appropriate neural network architecture that enables it to perform its described function, e.g., an architecture that includes one or more fully-connected neural network layers, convolutional neural network layers, pooling neural network layers, self-attention neural network layers, or a combination thereof. An attribute prediction neural network may be trained using appropriate neural network training techniques, e.g., stochastic gradient descent.

In a particular example, the scoring engine 414 may use an attribute prediction neural network to generate the binding score between: (i) the alternative protein, and (ii) a binding target that includes a target protein, using a binding prediction neural network. The binding prediction neural network may be configured to process respective representations of: (i) the predicted structure 420 of the alternative protein, and (ii) the (predicted) structure of the target protein, to generate the binding score for the alternative protein and the target protein.

At each optimization iteration, the update engine 416 determines whether to update the current amino acid sequence 408 to the alternative amino acid sequence 418 based on the respective design scores 426 for: (i) the alternative amino acid sequence 418, and (ii) the current amino acid sequence 408. The system 400 may have previously determined the design score for the current amino acid sequence 408, i.e., at the iteration where the current amino acid sequence 408 was generated, and thereafter maintained the design score for the current amino acid sequence. Therefore, rather than regenerating the design score for the current amino acid sequence 408 at the current iteration, the system 400 may retrieve and use the previously generated design score for the current amino acid sequence 408.

The update engine 416 may determine whether to update the current amino acid sequence 408 to the alternative amino acid sequence 418 using a simulated annealing optimization technique. More specifically, the update engine 416 may determine an "acceptance probability", e.g., represented as a numerical value in the range [0,1], that defines a likelihood for updating the current amino acid sequence 408 to the alternative amino acid sequence 418. The update engine 416 then updates the current amino acid sequence 408 to the alternative amino acid sequence 418 with probability defined by the acceptance probability.

The update engine 416 may determine the acceptance probability based on: (i) a "temperature" parameter (which may be represented as a numerical value), (ii) the design score for the current amino acid sequence 408, and (iii) the design score for the alternative amino acid sequence 418. Generally, higher values of the temperature parameter may cause the system 400 to implement a more "exploratory" optimization policy, while lower values of the temperature parameter may cause the system 400 to implement a more "greedy" optimization policy. For example, for a high value of the temperature parameter, the update engine 416 may determine a high acceptance probability even if the design score for the alternative amino acid sequence 418 is inferior to (e.g., lower than) the design score for the current amino acid sequence 408. In one example, the update engine 416 may determine the acceptance probability a as:

$$a = \begin{cases} 1 & \text{if } d' > d \\ \exp\left(\frac{d' - d}{T + \epsilon}\right) & \text{otherwise} \end{cases} \quad (1)$$

where d' denotes the design score for the alternative amino acid sequence 418, d denotes the design score for the current amino acid sequence 408, where a higher design score for an amino acid sequence indicates that the protein specified by the amino acid sequence better satisfies the design criteria, T denotes the temperature parameter, and e denotes a small positive constant to improve numerical stability. Other techniques for determining the acceptance probability are possible, and the technique defined by equation (4) is provided for illustrative purposes only.

The system 400 may determine that the current optimization iteration is the final optimization iteration once a termination criterion is satisfied, e.g., once a predetermined number of optimization iterations have been performed, or once the design score for the current amino acid sequence achieves (e.g., exceeds) a predefined threshold.

After the final optimization iteration, the system 400 selects an amino acid sequence generated during the optimization, i.e., at one of the optimization iterations, as the output amino acid sequence 404 specifying the protein 406. For example, the system 400 may select the current amino acid sequence at the final optimization iteration as the output amino acid sequence 404. As another example, the system 400 may select the amino acid sequence having the best (e.g., highest) design score among all the amino acid sequences generated during the optimization as the output amino acid sequence 404.

In some cases, rather than selecting a single output amino acid sequence 404, the system 400 may select multiple output amino acid sequences 404 specifying respective proteins 406. For example, the system 400 may select a predefined number of amino acid sequences having the best (e.g., highest) design scores from among all the amino acid sequences generated during the optimization as respective output amino acid sequences 404.

Optionally, the system 400 may repeatedly perform the optimization procedure to generate multiple output amino acid sequences, each of which may be different, e.g., due to randomness in the way the amino acid sequence is initialized at the first iteration, or due to randomness during the optimization procedure. The randomness during the optimization procedure may arise, e.g., by probabilistically determining whether the current amino acid sequence 408 should be updated at each iteration, as described above.

Generally, the protein 406 specified by the output amino acid sequence 404 generated by the system 400 may not strictly satisfy some, or any, of the protein design criteria that defined the optimization performed by the system 400. The protein 406 may not strictly satisfy all the protein design criteria, e.g., because biochemical constraints may prevent the protein from strictly satisfying the design criteria, or because the optimization performed by the system 400 may have converged to an undesirable local optimum of the design scores.

A protein having the output amino acid sequence 404 generated by the system 400 may be experimentally synthesized and validated, e.g., to determine by physical experiments whether the synthesized protein actually achieves the design criteria provided to the system 400. Proteins designed by the system 400 can be used for any of a variety of practical applications, e.g., as drugs to be administered to patients to achieve therapeutic effects, or as enzymes to catalyze industrial processes.

Figure 5:
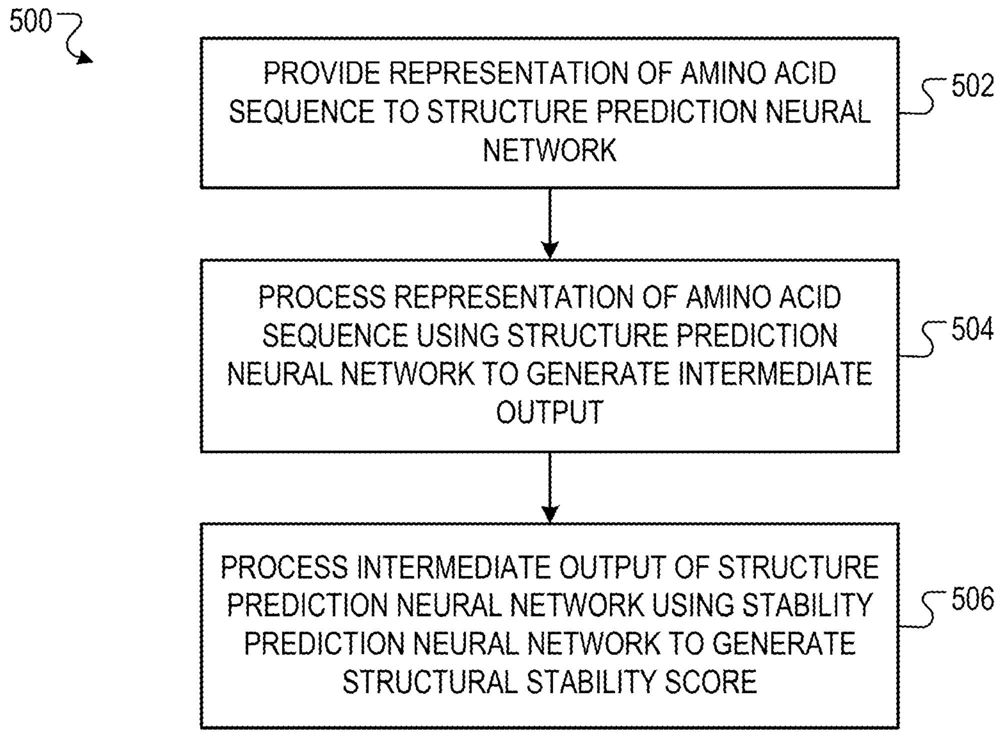
FIG. 5 is a flow diagram of an example process for predicting structural stability of a protein specified by an amino acid sequence.

FIG. 5 is a flow diagram of an example process 500 for predicting structural stability of a protein specified by an amino acid sequence. For convenience, the process 500 will be described as being performed by a system of one or more computers located in one or more locations. For example, a protein stability prediction system, e.g., the protein stability prediction system 100 of FIG. 1, appropriately programmed in accordance with this specification, can perform the process 500.

The system provides a representation of the amino acid sequence of the protein to a structure prediction neural network (502). The structure prediction neural network is configured to process a representation of an input amino acid sequence to generate an output characterizing a predicted structure of a protein specified by the input amino acid sequence.

The system processes the representation of the amino acid sequence of the protein using the structure prediction neural network, in accordance with current values of structure prediction neural network parameters, to generate an intermediate output of the structure prediction neural network (504). The intermediate output of the structure prediction neural network includes an output generated by one or more hidden layers of the structure prediction neural network.

The system processes the intermediate output of the structure prediction neural network using a stability prediction neural network, in accordance with current values of stability prediction neural network parameters, to generate a predicted structural stability score characterizing the predicted structural stability of the protein specified by the amino acid sequence (506).

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A method performed by one or more computers, the method comprising:

processing an input comprising a representation of an amino acid sequence of a protein using a structure prediction neural network, in accordance with current values of structure prediction neural network parameters, to generate an intermediate output of the structure prediction neural network that defines an embedding of the amino acid sequence of the protein, wherein the structure prediction neural network is configured through training by a machine learning training technique to process a representation of an input amino acid sequence to generate an output characterizing a predicted structure of a protein specified by the input amino acid sequence, wherein the intermediate output of the structure prediction neural network comprises an output generated by one or more hidden layers of the structure prediction neural network;

processing the embedding of the amino acid sequence of the protein that is defined by the intermediate output of the structure prediction neural network using a stability prediction neural network, in accordance with current values of stability prediction neural network parameters, to generate a predicted structural stability score characterizing the predicted structural stability of the protein specified by the amino acid sequence; and training the stability prediction neural network to reduce an error in the predicted structural stability score, comprising:

determining gradients of the error with respect to the current values of the stability prediction neural network parameters and the structure prediction neural network parameters, comprising backpropagating gradients of the error through the stability prediction neural network and into the structure prediction neural network; and updating the current values of the stability prediction neural network parameters and the structure prediction neural network parameters using the gradients.

2. The method of claim 1, further comprising:

determining gradients of the predicted structural stability score with respect to the representation of the amino acid sequence; and using the gradients of the predicted structure stability score with respect to the representation of the amino acid sequence to update the amino acid sequence.

3. The method of claim 2, wherein determining gradients of the predicted structural stability score with respect to the representation of the amino acid sequence comprises:

backpropagating gradients of the predicted structural stability score through both the stability prediction neural network and the structure prediction neural network.

4. The method of claim 2, wherein using the gradients of the predicted structural stability score with respect to the representation of the amino acid sequence to update the amino acid sequence comprises:

updating the amino acid sequence to encourage an increase in a structural stability of the protein specified by the amino acid sequence.

5. The method of claim 2, wherein using the gradients of the predicted structural stability score with respect to the representation of the amino acid sequence to update the amino acid sequence comprises:

updating the amino acid sequence to encourage a decrease in a structural stability of the protein specified by the amino acid sequence.

6. The method of claim 2, wherein using the gradients of the predicted structural stability score with respect to the representation of the amino acid sequence to update the amino acid sequence comprises:

updating the amino acid sequence to encourage a structural stability of the protein specified by the amino acid sequence to match a target structural stability.

7. The method of claim 2, further comprising making the protein specified by the amino acid sequence.

8. The method of claim 1, further comprising:

determining, based at least in part on the predicted structural stability score, that the protein specified by the amino acid sequence satisfies a design criterion; and providing an output that specifies the amino acid sequence.

9. The method of claim 1, further comprising determining the amino acid sequence of a physical protein molecule, and predicting the structural stability of the physical protein molecule specified by the determined amino acid sequence by generating the predicted structural stability score for the physical protein molecule specified by the determined amino acid sequence.

10. The method of claim 1, wherein the intermediate output of the structure prediction neural network comprises features characterizing the amino acid sequence of the protein.

11. The method of claim 1, wherein the input comprising the representation of the amino acid sequence of the protein comprises a respective embedding of an amino acid in each position of the amino acid sequence.

12. A system comprising:

one or more computers; and one or more storage devices communicatively coupled to the one or more computers, wherein the one or more storage devices store instructions that, when executed by the one or more computers, cause the one or more computers to perform operations comprising:

processing an input comprising a representation of an amino acid sequence of a protein using a structure prediction neural network, in accordance with current values of structure prediction neural network parameters, to generate an intermediate output of the structure prediction neural network that defines an embedding of the amino acid sequence of the protein, wherein the structure prediction neural network is configured through training by a machine learning training technique to process a representation of an input amino acid sequence to generate an output characterizing a predicted structure of a protein specified by the input amino acid sequence, wherein the intermediate output of the structure prediction neural network comprises an output generated by one or more hidden layers of the structure prediction neural network;

processing the embedding of the amino acid sequence of the protein that is defined by the intermediate output of the structure prediction neural network using a stability prediction neural network, in accordance with current values of stability prediction neural network parameters, to generate a predicted structural stability score characterizing the predicted structural stability of the protein specified by the amino acid sequence; and training the stability prediction neural network to reduce an error in the predicted structural stability score, comprising:

determining gradients of the error with respect to the current values of the stability prediction neural network parameters and the structure prediction neural network parameters, comprising backpropagating gradients of the error through the stability prediction neural network and into the structure prediction neural network; and updating the current values of the stability prediction neural network parameters and the structure prediction neural network parameters using the gradients.

13. One or more non-transitory computer storage media storing instructions that when executed by one or more computers cause the one or more computers to perform operations comprising:

processing an input comprising a representation of an amino acid sequence of a protein using a structure prediction neural network, in accordance with current values of structure prediction neural network parameters, to generate an intermediate output of the structure prediction neural network that defines an embedding of the amino acid sequence of the protein, wherein the structure prediction neural network is configured through training by a machine learning training technique to process a representation of an input amino acid sequence to generate an output characterizing a predicted structure of a protein specified by the input amino acid sequence, wherein the intermediate output of the structure prediction neural network comprises an output generated by one or more hidden layers of the structure prediction neural network;

processing the embedding of the amino acid sequence of the protein that is defined by the intermediate output of the structure prediction neural network using a stability prediction neural network, in accordance with current values of stability prediction neural network parameters, to generate a predicted structural stability score characterizing the predicted structural stability of the protein specified by the amino acid sequence; and training the stability prediction neural network to reduce an error in the predicted structural stability score, comprising:

determining gradients of the error with respect to the current values of the stability prediction neural network parameters and the structure prediction neural network parameters, comprising backpropagating gradients of the error through the stability prediction neural network and into the structure prediction neural network; and updating the current values of the stability prediction neural network parameters and the structure prediction neural network parameters using the gradients.

14. The non-transitory computer storage media of claim 13, wherein the operations further comprise:

determining gradients of the predicted structural stability score with respect to the representation of the amino acid sequence; and using the gradients of the predicted structure stability score with respect to the representation of the amino acid sequence to update the amino acid sequence.

15. The non-transitory computer storage media of claim 14, wherein determining gradients of the predicted structural stability score with respect to the representation of the amino acid sequence comprises:

backpropagating gradients of the predicted structural stability score through both the stability prediction neural network and the structure prediction neural network.

16. The non-transitory computer storage media of claim 14, wherein using the gradients of the predicted structural stability score with respect to the representation of the amino acid sequence to update the amino acid sequence comprises:

updating the amino acid sequence to encourage an increase in a structural stability of the protein specified by the amino acid sequence.

17. The non-transitory computer storage media of claim 14, wherein using the gradients of the predicted structural stability score with respect to the representation of the amino acid sequence to update the amino acid sequence comprises:

updating the amino acid sequence to encourage a decrease in a structural stability of the protein specified by the amino acid sequence.

18. The non-transitory computer storage media of claim 14, wherein using the gradients of the predicted structural stability score with respect to the representation of the amino acid sequence to update the amino acid sequence comprises:

updating the amino acid sequence to encourage a structural stability of the protein specified by the amino acid sequence to match a target structural stability.

19. The non-transitory computer storage media of claim 13, wherein the operations further comprise:

determining, based at least in part on the predicted structural stability score, that the protein specified by the amino acid sequence satisfies a design criterion; and providing an output that specifies the amino acid sequence.

20. The non-transitory computer storage media of claim 13, wherein the operations further comprise determining the amino acid sequence of a physical protein molecule, and predicting the structural stability of the physical protein molecule specified by the determined amino acid sequence by generating the predicted structural stability score for the physical protein molecule specified by the determined amino acid sequence.

* * * * *